United States Patent [19]

Evans, II et al.

[11] Patent Number: 5,193,547
[45] Date of Patent: Mar. 16, 1993

[54] UNIVERSAL CONNECTOR MEANS FOR TRANSDUCER/MONITOR SYSTEMS

[76] Inventors: George D. Evans, II, 9625 Wichita Dr., Arlington, Calif. 92503; Jacob J. Norman, 14331 Riverton Cir., Westminster, Calif. 92683; H. Don Phillips, 1329 Crofton Ct., Upland, Calif. 91781

[21] Appl. No.: 945,381

[22] Filed: Dec. 22, 1986

Related U.S. Application Data

[63] Continuation of Ser. No. 830,546, Feb. 18, 1986, abandoned, which is a continuation of Ser. No. 629,892, Jul. 16, 1984, abandoned.

[51] Int. Cl.$^5$ .............................................. A61B 5/00
[52] U.S. Cl. ...................................... 128/668; 128/673; 128/748
[58] Field of Search ............... 128/900, 902, 673, 675, 128/748, 668; 330/1 R; 323/911

[56] References Cited

U.S. PATENT DOCUMENTS

| | | | |
|---|---|---|---|
| 3,602,215 | 8/1971 | Parnell | 128/902 |
| 3,721,230 | 3/1973 | Ziernicki | 128/902 |
| 3,868,679 | 2/1975 | Arneson | 128/673 |
| 3,986,495 | 10/1976 | Miller | 323/911 |
| 4,003,370 | 1/1977 | Emil et al. | 128/673 |
| 4,066,974 | 1/1978 | Reinhard | 128/902 |
| 4,206,762 | 6/1980 | Cosman | 128/675 |
| 4,213,348 | 7/1980 | Reinertson et al. | 324/130 |
| 4,243,044 | 1/1981 | Blancke | 128/902 |
| 4,297,890 | 11/1981 | Hök | 128/673 |
| 4,325,382 | 4/1982 | Miodownik | 128/673 |
| 4,598,281 | 7/1986 | Maas | 128/902 |
| 4,611,601 | 9/1986 | Bowman | 128/673 |

OTHER PUBLICATIONS

"New Instrumentation Amplifiers for Electrical & Non Electrical Variables", by Sima Siemans Review XXXIX (1972) No. 2, pp. 75–77.
"An Improved Systolic–Diastolic Pulse Separator", by Francis, Med. & Biol. Eng. vol. 12, No. 1 (Jan. 1974) pp. 105–108.
"Batteryless On–Demand–Sampling Active Radiosonde for Intracranial Pressure Measurement", by Macellari; Med. & Biol. Eng. & Comput vol. 14, No. 6 (Nov. 1981) pp. 686–694.
"Oscilloscope . . . Measurements", by Caldwell et al.; Med. & Biol. Eng. Jun. 1973, pp. 500–503.
1980 Linear Databook by National Semiconductor, pp. 4–19 & 4–31.
"Biomedical . . . Circuits", by Scott et al.; Med. & Biol. Eng.; vol. 14 #6; Nov. 1976, pp. 684–687.
"Versitile . . . Muscles", by Corinth; Elektroniks; vol. 23, #7; pp. 247–250 & 265.

*Primary Examiner*—David M. Shay
*Attorney, Agent, or Firm*—Lynn & Lynn

[57] ABSTRACT

A system for monitoring physiological conditions in humans and other animals includes a transducer for monitoring such conditions as blood pressure, a monitor for displaying or recording signals from such transducers, or both, and a connector for linking the transducer to the monitor and for transforming the impedance level of signals from such transducer to levels appropriate for such monitors and for drawing and adapting power from the monitor for effecting this impedance transformation. The connector may also include a mechanism for adjusting the offset or sensitivity of the signal from the transducer, a mechanism for detecting the absence of the transducer, and a mechanism for detecting an open circuit between the monitor and the transducer. A connector may also include a device for converting power drawn from a monitor to direct current where the power drawn from the monitor is, before conversion, either sine wave or pulsed; a mechanism for regulating the current from the monitor; and a mechanism for eliminating common-mode voltage errors from the transducer signal.

6 Claims, 4 Drawing Sheets

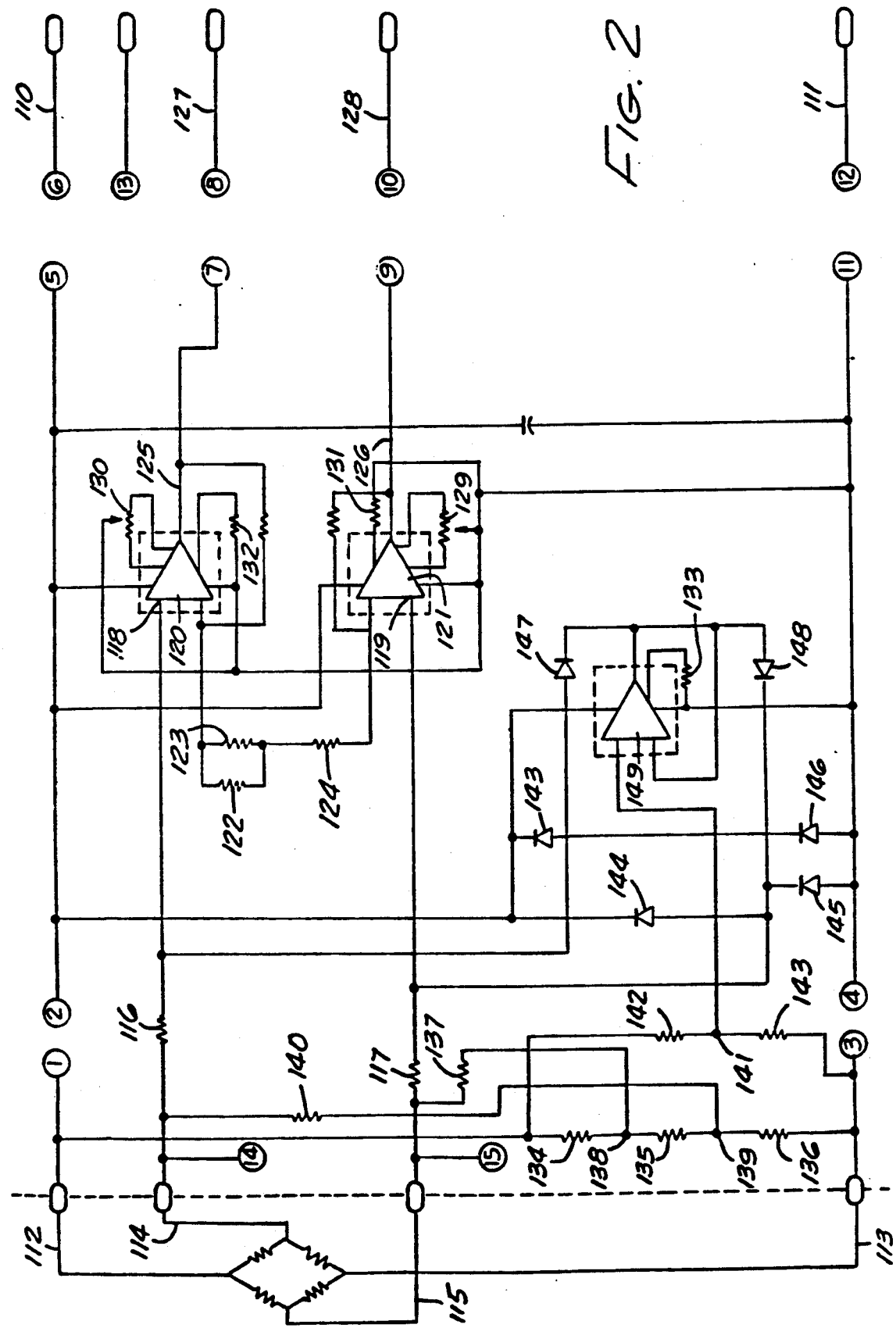

UNIVERSAL CONNECTOR MEANS FOR TRANSDUCER/MONITOR SYSTEMS

This is a continuation of co-pending application Ser. No. 830,546 filed on Feb. 18, 1986, now abandoned; which is a continuation of application Ser. No. 629,892 filed on Jul. 16, 1984, now abandoned.

This invention elates to systems for detecting blood pressure un humans, for converting the detected blood pressure into electrical signals, and for displaying, recording or otherwise monitoring these electrical signals promptly after detection. Such systems include a blood-pressure transducer that is attached to he arterial or venous system of a human, a blood-pressure monitor that indicates blood pressure, and our new, universal connector/cable assembly, the connector. The connector is compatible with many different types of blood-pressure transducers and with many different kinds of blood-pressure monitors.

In general, the input-output transfer function of a system is affected by the conditions existing at he input and output ports, so that a meaningful specification of the transfer function must also includes statement as to what these conditions are. In a pump, for example, the throughput may well be affected by changes in pressure at the input and output ports. Thus, a proper specification of the performance should include graphs showing the variation of throughput with input and output port pressures. In a generalized system these pressures correspond to the input and output load conditions.

To avoid errors arising from improper matching between systems, it is essential that the terminal properties of each component system be properly understood. Mismatch errors commonly take the form of a frequency-dependent signal attenuation, but under extreme conditions nonlinear distortion can also occur. While attenuation between parts of a system arising from improper matching can usually be corrected, improper matching between the signal source and the transducer can be especially troublesome when the source impedance is unstable. The reason for this is simply that it becomes impossible to distinguish whether an apparent signal variation is caused by a source impedance variation or a true signal variation. In such a situation it is important to design the transducer in such a way that its effect on the signal source can be neglected.

Quantities that conveniently characterize the input and output properties of most systems are the generalized input impedance and output impedance. Although these quantities are usually associated with purely electrical systems, they can also be conveniently applied to mechanical and hydraulic systems. Thus, one speaks of the mechanical input and output impedances. Formally, the generalized impedance Z is defined by $Z = $ Generalized effort/Generalized flow which, in general, is a complex quantity, since the effort and flow may be out of phase. Thus, Z has a magnitude and phase values of which may be frequency-dependent.

For an electrical system, Z is the ratio of the voltage to the current, and the input impedance can be found by applying a known sinusoidal emf to the input and measuring the input current. Similarly the output impedance can be found by applying an emf to the output terminals and measuring the output current.

That is, the invention relates to systems for detecting physiological conditions in humans or other animals, for converting the detected physiological conditions into electrical signals, and for displaying, recording or otherwise monitoring these electrical signals promptly after detection. The transducer can detect such physiological conditions as temperature, blood gas levels and hematocrit levels. Our new, universal connector/cable assembly, is compatible with many different kinds of transducers and monitors.

Heretofore, no such connector for transducers and monitors such as those for blood pressure has been available. As a result, patients whose blood pressure requires monitoring have suffered the risks of medical diagnosis or treatment without such monitoring during an exchange from one transducer to another each time someone wanted to monitor blood pressure on a monitor incompatible with the patient's first blood-pressure transducer.

Our new connector permits linking a wide variety of transducers to a wide variety of monitors. For example, this connector is compatible with many different kinds of blood pressure transducers, including disposable and reusable transducers, and with a wide variety of commercially available blood-pressure monitors. The connector can be adapted for use with monitors such as blood-pressure monitors, that provide power to a transducer in the form of DC voltage, sine wave voltage, or pulsed voltage, for example, square wave voltage having a duty cycle of about 50%. The connector in preferred embodiment is then linked to one monitor or to a group of monitors whose power systems are compatible with the connector as adapted. The monitor/connector combination can then be linked to the electrical output of a plurality of different kinds of transducers, thus avoiding the risks of contamination often arising when a transducer is decoupled from the lines leading into a patient's bloodstream.

The new universal connector means of this invention includes means for transforming the impedance level of a signal from a physiological condition transducing means to the input impedance of monitoring means, and means for drawing and adapting power from the monitoring means for effecting the impedance transformation.

The universal connector means can accommodate a wide range of transducer output impedance. For example, the connector can accommodate signals from blood-pressure transducers having output impedances in the range of about 50 to about 8,000 ohms. The connector can also accommodate and adjust to input impedance levels appropriate for many different monitors. For example, the connector can accommodate monitors that having output impedance in the range of about 5 ohms to about one million ohms.

Our connector permits display and monitoring of signals from two or more different types of transducers. This display maybe monitored on displays designed for only one or two types of transducer signals. For example, our connector permits matching the impedance level of a blood gas level transducer to that of a monitor designed for displaying blood pressure.

Our new connector can also link monitors with means for receiving and demodulating signals representing physiological conditions. Such receiving/demodulating means can be a radio frequency receiver/demodulator for signals from an RF modulator/transmitter.

Our new universal connector may also include means for adjusting offset or sensitivity of the signal from the blood-pressure transducing means, means for detecting absence of the transducing means, and means for detecting an open circuit between the transducing means and the monitoring means, when features of the monitor to be linked to the transducer require them.

As needed, our new universal connector may also include means for converting power from the monitoring means to DC power where the power from the monitoring means, before conversion, is a sine wave or a pulsed voltage such as a square wave having a duty cycle of about 50%. Where necessary, our new connector may also include means for regulating the current from the monitoring means, and means for eliminating erroneous common-mode voltages and for imposing appropriate common-mode voltages compatible with a given monitoring means.

Our new universal connector is particularly useful with blood-pressure transducers made by American Bentley, a subsidiary of American Hospital Supply Corporation. Among the Bentley transducers that are compatible with the new universal connector are Bentley transducer Models BT800B, BTX600, BTX700, BT900B, BT1000, and BTX1000.

Among the many kinds of blood-pressure monitors compatible with our new universal connector are the following: Hewlett-Packard monitors; Tektronix/-Vitatek monitors; General Electric/Marquette PDS-3000 monitors; Spacelabs monitors; Datascope 870 monitors; and others.

In preferred embodiment, our new universal connector includes two circuit assemblies mounted back-to-back. In these preferred embodiments, one circuit is designated the buffer-amplifier circuit; the other, the DC power supply circuit, current-regulating circuit, or common-mode eliminator circuit. The two circuits are linked by appropriate means (e.g., bus wire) and are selected to be compatible with the transducer and monitor in our system.

Our new system, and the new universal connector of our system, can better be understood by reference to the drawings, in which:

FIG. 2 is a detailed schematic of the preferred embodiment of the buffer-amplifier circuit in the new universal connector;

Figure 1:
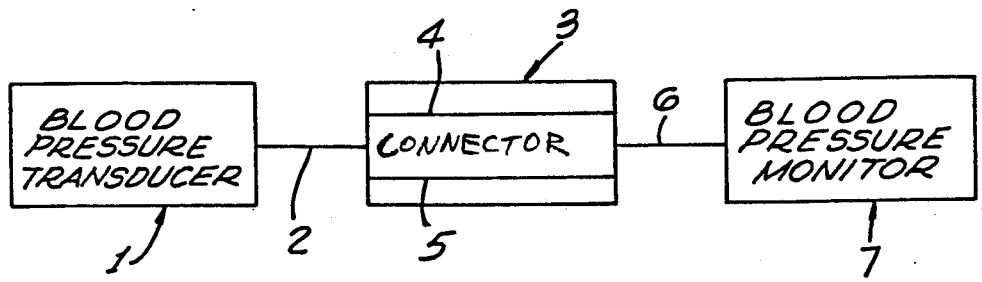
FIG. 1 is a block diagram of our system including a blood-pressure transducer, our new universal connector, and a blood-pressure monitor.

FIG. 1 provides a block diagram of our new system, including blood-pressure transducer 1 linked to blood-pressure monitor 7 by cables 2 and 6 and by our new universal connector 3. Connector 3 includes buffer-amplifier circuit board 4 linked to circuit board 5, which includes either a DC power supply circuit, a current-regulating circuit, or a common-mode elimination circuit.

FIG. 2 provides a detailed schematic of the preferred embodiment of our buffer-amplifier circuit. This circuit draws power from the blood-pressure monitoring means, and utilizes that power directly where the power is DC. Another circuit is used to modify and adapt the power if the power is sine wave or pulsed (see FIG. 3). The left side of the buffer-amplifier circuit is linked to the blood-pressure transducing means; the right side, to the blood-pressure monitoring means. On the right side of the schematic, positive and negative excitation pass from the monitoring means on paths 110 and 111 through contacts 6 and 12 to the other circuit in the connector means (described below) and return to the buffer-amplifier circuit, adapted as necessary, through contact pairs 5/11, 2/4, and 1/3. The excitation current then flows to the transducer along paths 112 and 113.

Signals representative of blood pressure pass from the transducer means on paths 114 and 115 with their negative side on path 115, and their positive side, on path 114. These signals pass through protective resistors 116 and 117 to input rails 118 and 119 on amplifiers 120 and 121, respectively. The diffential gain through amplifiers 120 and 121 is approximately one unless gain-setting resistors 122–124 are present. Normally, only an impedance level conversion takes place as the signals undergo buffering through amplifiers 120 and 121. For example, a common transducer output impedance is between 300 and 5,000 ohms; amplifier output impedance is in the range of about 1 to about 5 ohms.

Output signals emerging from amplifiers 120 and 121 on paths 125 and 126, respectively, pass to the other circuit boards through contacts 7 and 9. Where the other circuit is a DC power supply circuit or current-regulating circuit, these signals pass through output resistors which provide impedance matching for the monitor in the system. If the other circuit is a common-mode eliminator, the signals are passed through circuitry and then through output resistors to the monitor. From the output resistors, the signals return to the first circuit board through contacts 8 and 10, and then pass to the monitor on paths 127 and 128.

The buffer-amplifier circuit includes means for removing offset errors in the signal voltage to the monitoring means. Adjustment of potentiometers 129 (on amplifier 121) and 130 (on amplifier 120) permit setting the output voltages of these amplifiers at the same level as their input voltages.

Gain-setting resistors 122, 123 and 124 permit accurate gain tailoring. Resistors 131, 132 and 133 permit adjustment of amplifier bandwidth when programmable amplifiers are used.

The buffer-amplifier circuit of FIG. 2 also includes means for detecting a missing transducer or an open lead. Two resistor dividers are used to develop reference voltages. Resistors 134, 135 and 136 develop two voltages referenced to the magnitude of the transducer excitation voltage. The voltage at junction 138 of resistors 134, 135 and 137 is more than half the instantaneous transducer voltage; the voltage at junction 139 of resistors 135, 136 and 140 is less than half of the instantaneous transducer excitation voltage, and common-mode voltage from the transducer is about 50% of excitation voltage. Accordingly, the voltage at junction 141 of resistors 142 and 143 is about half the excitation voltage.

In normal operation, the detection circuitry has little effect upon signal paths because resistors 137 and 140 are large compared with transducer output resistance, and because diodes 143-148 are reverse biased. If no transducer is present, however, resistors 137 and 140 are small compared to the input impedance of amplifiers 120 and 121. The resulting large reverse polarity signal at the blood-pressure monitor indicates the absence of a transducer.

If a transducer is present, but one or both signal paths 114 and 115 are open between transducers and amplifiers 120 and 121, the effects upon the signal and blood-pressure monitor would be the same as those described above.

If a transducer is present, but one of the excitation leads to the transducer is open, the reverse reference voltage operating through resistor 137 and 140 has no impact on the signal because of the low output impedance of the transducer for example, if the negative excitation line is open, signals on paths 114 and 115 will be pulled toward the positive excitation voltage by current through the transducer. As the signals become more positive, diode 147 becomes forward biased. The signal at the inboard side of resistor 116 is clamped at one diode drop above the output of amplifier 149. The signal at resistor 117 continues to rise, almost to the level of the positive excitation voltage. The resulting large negative signal appearing at the monitor indicates the error. The same occurs where the positive excitation line is open, and the negative line is connected. If both the positive and negative lines are open, and both paths 114 and 115 are connected to amplifiers 120 and 121, a much smaller negative signal will appear at the monitoring means.

Figure 3:
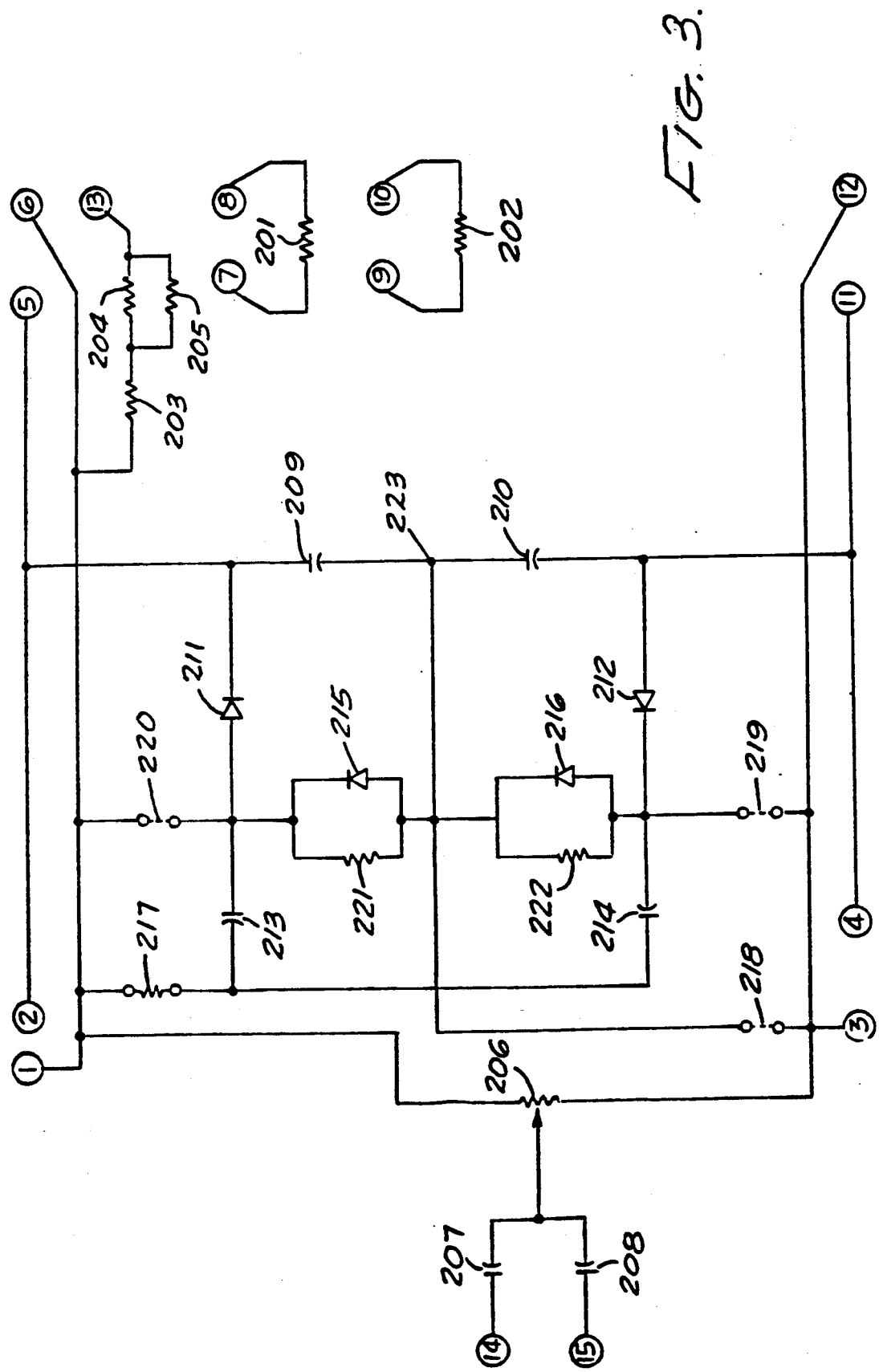
FIG. 3 is a detailed schematic of a DC power supply circuit, for use as needed, in our new universal connector.

FIG. 3 provides a detailed schematic of a DC power supply circuit. This circuit performs four functions.

First, output resistors 201 and 202 are matched or adjusted to the input impedance requirement of the monitoring means. Output signals from a buffer-amplifier circuit of FIG. 2 appear at contacts 7 and 9 and return to the buffer-amplifier circuit through contacts 8 and 10.

Secondly, where calibration resistance is required, resistor network 203, 204 and 205 provides this function. A calibration signal passes through the buffer-amplifier circuit through contact 13.

Third, this circuit provides sine wave phase correction through the network including potentiometer 206 and capacitors 207 and 208. Unbuffered signals from the transducer pass to sine wave phase correction through contacts 14 and 15.

The fourth and most important function of the circuit in FIG. 3 is conversion of sine wave or pulsed excitation signals to DC voltage suitable for operating the buffer-amplifier circuit. To accommodate the various types of excitation signals, the components in the circuit are varied and tailored as needed.

For sine wave conversion, this circuit includes capacitors 209, 210, 213 and 214 to hold voltage levels; diodes 211, 212, 215 and 216 for reverse biasing protection; resistor 217; and jumper wire 218. Omitted are jumper wires 219 and 220 and resistors 221 and 222.

The negative excitation signal from the monitoring means is used as a reference, and is connected to junction 223 via jumper wire 218. The upper and lower halves of this circuit then function as two separate converters, with each functioning as a voltage doubler. The upper half produces a positive voltage; the lower half a negative voltage, with respect to the negative excitation signal. Capacitor values are appropriate to produce low-ripple DC voltage.

The upper half of the circuit functions as follows. Assume that the excitation voltage is a sine wave from a transformer. Assume that the negative excitation voltage from the monitoring means is a reference voltage, and that all voltages in the power supply are defined with respect to this reference. Total excitation voltage is applied to each half of the circuit independently. As the negative half-cycle of the positive excitation signal from the monitoring means is applied to capacitor 213, current flows from the reference through diode 215 to charge the positive side of the capacitor 213 to approximately reference potential. The negative side of capacitor 213 is charged with a negative peak of the positive excitation signal. Therefore, capacitor 213 holds a voltage approximating the peak excitation voltage. As the positive excitation sine wave goes from a negative to a positive peak with respect to the reference, the voltage on both sides of capacitor 213 changes by the same amount. The negative side of capacitor 213 changes from negative excitation peak to positive excitation peak. The positive side changes from the reference voltage to twice the positive excitation peak less the diode drop. The voltage on the positive side of capacitor 213 also causes diode 211 to become forward biased. Current then flows into the positive side of capacitor 209. Capacitor 209 is charged to a voltage that approximates double the positive excitation voltage peak minus two diode drops. Operation of the other half of the supply is the same, but polarity is reversed.

Where the power from the monitoring means is a symmetrical pulse excitation, the circuitry in FIG. 3 is configured as follows. Capacitors 209 and 210, and diodes 211 and 212 remain in circuit with resistors 221 and 222 and jumper wires 220 and 219. Capacitors 213 and 214, diodes 215 and 216, resistor 217 and jumper wire 218 are omitted. With symmetrical waveforms, the excitation voltages are applied across both halves of the circuit in series. Where no pulse is present, both diodes 211 and 212 are back biased. When simultaneous pulses appear, these diodes conduct, and capacitors 209 and 210 receive charging current. The final voltage developed in capacitors 209 and 210 in series is approximately twice the pulse amplitude minus the drops across the diodes 211 and 212.

Excitation voltage passes from the circuitry of FIG. 2 to contacts 6 and 12, and returns to the buffer-amplifier circuit unaltered through contacts 1 and 3. DC power returns to the buffer-amplifer circuit through contacts 2, 4, 5 and 11.

Figure 4:
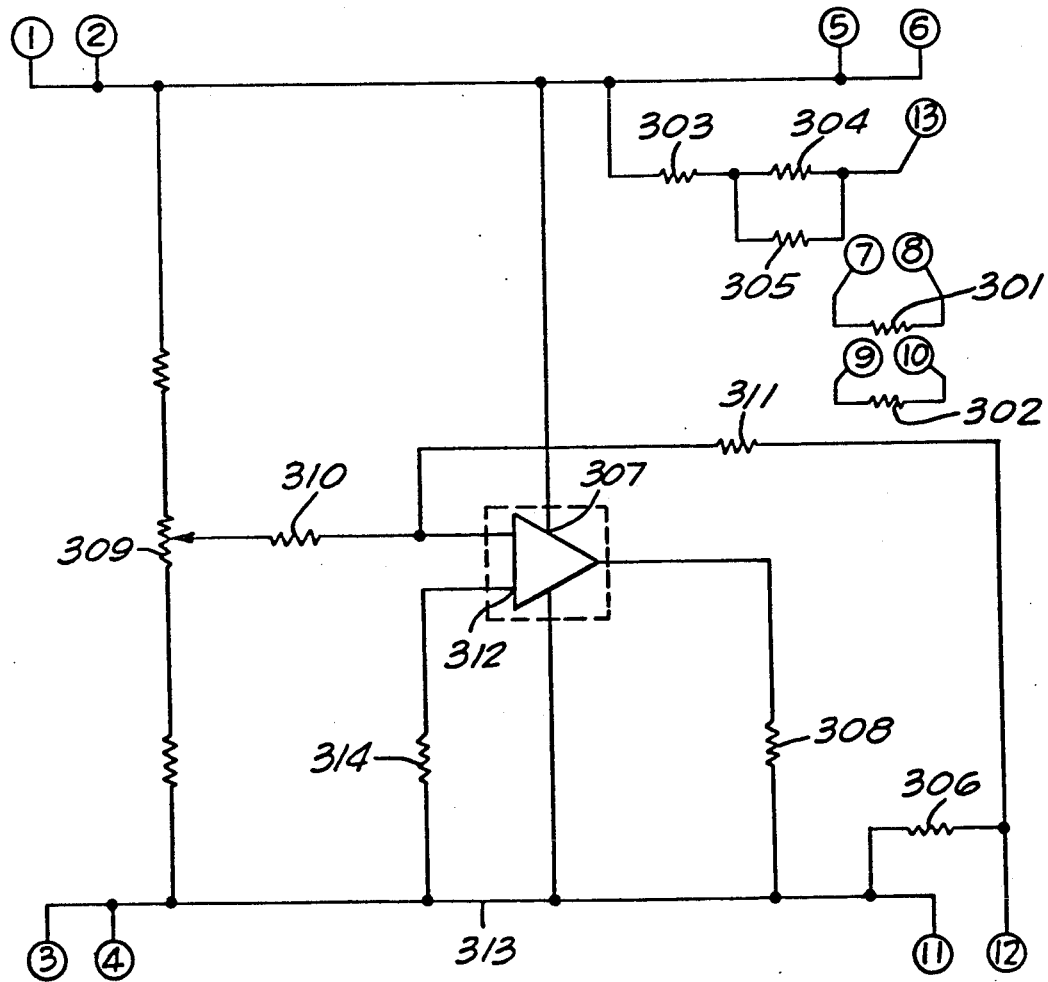
FIG. 4 is a detailed schematic of a current-regulating circuit, for use as needed in our new universal connector.

FIG. 4 illustrates the preferred embodiment of the current-regulating circuit that provides three functions. First, output resistors 301 and 302 serve the same functions as resistors 201 and 202 in the DC power circuit illustrated in FIG. 3.

Secondly, calibration resistors 303, 304 and 305 serve the same function as calibration resistors 203, 204 and 205 in the circuitry of FIG. 3.

Thirdly, this circuit provides current regulation. The total excitation load current, on leads 6 and 12, passes through resistor 306. Amplifier 307 samples the current at resistor 306, and varies amplifier output current through resistor 308, thus regulating current through resistor 306. Potentiometer 309 and resistor network 310/311 permit current trimming. (The reference voltage for amplifier 307 on negative rail 312 is the excitation voltage on path 313 applied through resistor 314.)

Figure 5:
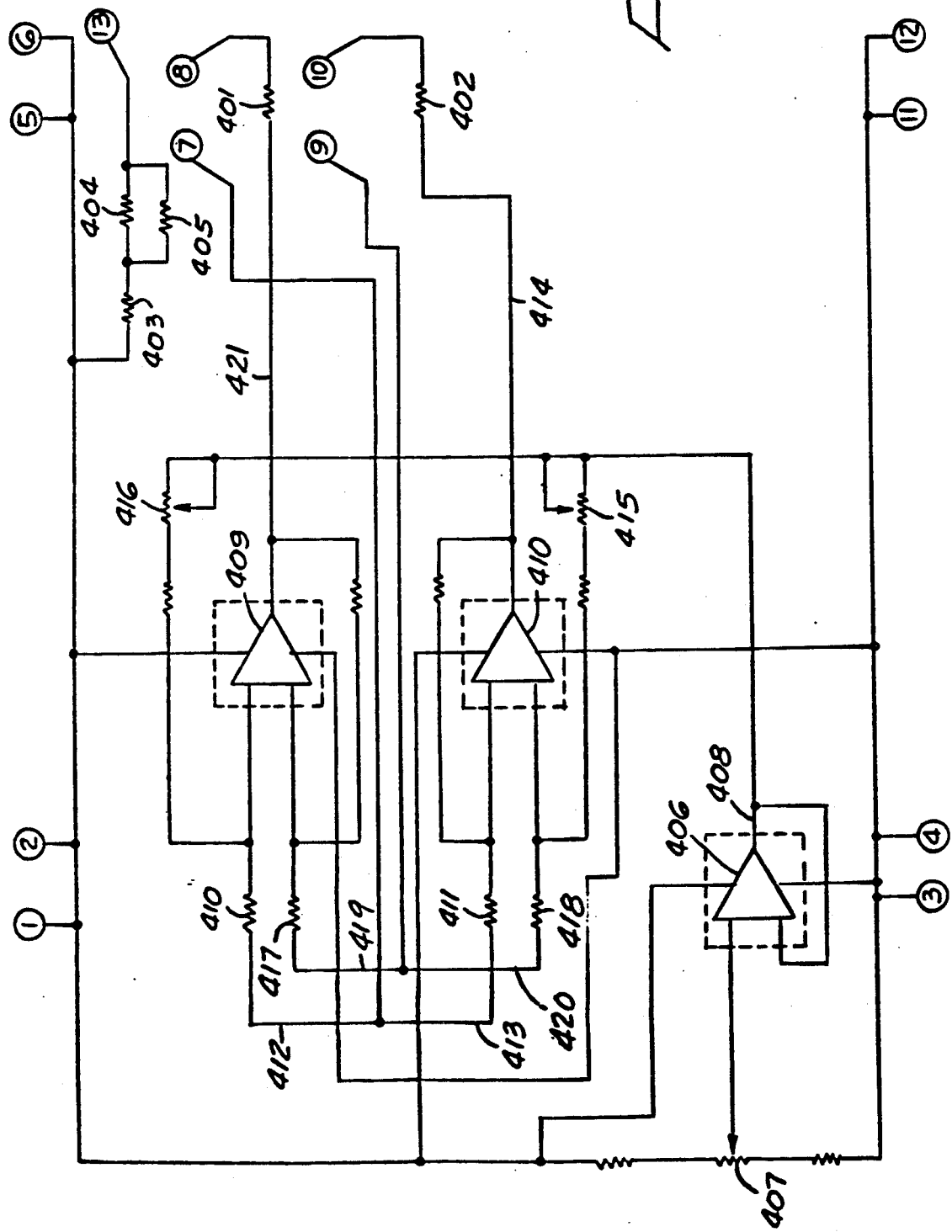
FIG. 5 is a detailed schematic of a circuit for eliminating an erroneous common-mode voltage from a transducer signal, for use as needed, in our new universal connector.

FIG. 5 provides a detailed schematic of a preferred embodiment for the common-mode eliminator circuit This circuit has three functions. First, resistors 401 and 402 are matched to the impedance requirements of the monitor, and function as resistor 301/302 and 201/202 of FIGS. 3 and 4 do. Secondly, calibration resistors 403, 404 and 405 serve the same functions as the calibration resistors illustrated in FIGS. 3 and 4.

The most important function of the circuitry in FIG. 5 is to remove an erroneous common-mode voltage from the transducer signal and substitute a proper common-mode voltage. Amplifier 406 and its related components provide the desired common-mode voltage, Potentiometer 407 is adjusted to obtain a voltage at the output 408 of amplifier 406 equal to half the excitation voltage This developed common-mode voltage then serves as the reference voltage for the differential amplifier circuit including amplifiers 409 and 410.

Buffered transducer signals pass from the buffer-amplifier circuit of FIG. 2 through contacts 7 and 9. The signal through contact 7 is applied to input resistors 410 and 411 along paths 412 and 413, respectively. The signal through contact 9 is applied to input resistors 417 and 418 along paths 419 and 420, respectively Corrected signals at outputs 421 and 414 pass through output resistors 401 and 402, respectively, and then through contacts 8 and 10 to the buffer-amplifier circuit shown in FIG. 2. Potentiometers 415 and 416 permit adjustment of the gain through amplifiers 409 410. Precise gain matching between two sides of the amplifiers is essential to maintain good common-mode rejection.

What is claimed is:

1. A system for use in environment having electromagnetic interference to monitor blood pressure in living tissue, comprising:
   a transducer for converting a blood pressure into an electrical signal, said transducer exhibiting an electrical output impedance;
   electrical signal monitoring means having an input electrical impedance different form said electrical output impedance; and
   electrical amplifying means having an input connected to the transducer and an output connected to the monitoring means, said input of said amplifying means having an impedance acceptability range including the electrical output impedance of the transducer and said output of said amplifying means having an output impedance compatible with the input impedance of the monitoring means.

2. A system for use in an environment having electromagnetic interference to monitor blood pressure in living tissue, comprising:
   blood pressure transducing means having an electrical output signal and a transducer output impedance;
   monitoring means having a monitor input impedance for monitoring signals from said blood pressure transducing means;
   means for interconnecting said blood pressure transducing means and said monitoring means, said interconnecting means including means for matching the output impedance of said transducer means to a value compatible with the input impedance of said monitoring means; and
   means for drawing power from said monitoring means for effecting said impedance matching.

3. The system of claim 2 wherein said blood pressure transducing means produces an output signal having an offset, said interconnecting means includes means for adjusting the offset of said blood pressure transducing means electrical output signal.

4. The system of claim 2 wherein the interconnecting means further comprises means for eliminating or minimizing common-mode voltage.

5. The system of claim 2 wherein the impedance of said blood pressure transducing means is in the range of about 50 to 8,000 ohms.

6. The system of claim 2 wherein the impedance of said blood pressure transducing means is in the range of about 50 to about one million ohms.

* * * * *